(12) United States Patent
Fleury

(10) Patent No.: US 7,863,568 B2
(45) Date of Patent: Jan. 4, 2011

(54) PHOTOSENSITIVE SENSOR IN THE AUTOMOTIVE FIELD

(75) Inventor: Benoist Fleury, Vincennes (FR)

(73) Assignee: Valeo Vision, Bobigny (FR)

( * ) Notice: Subject to any disclaimer, the term of this patent is extended or adjusted under 35 U.S.C. 154(b) by 0 days.

(21) Appl. No.: 11/940,614

(22) Filed: Nov. 15, 2007

(65) Prior Publication Data
US 2008/0111075 A1     May 15, 2008

(30) Foreign Application Priority Data
Nov. 15, 2006   (FR) ................... 06 09962

(51) Int. Cl.
*G01N 21/00* (2006.01)
(52) U.S. Cl. .......... 250/338.1; 348/E13.007; 348/E13.072; 396/121; 235/462.22; 250/575; 250/208.1
(58) Field of Classification Search ........ 340/602; 348/E13.007, E13.072; 623/6.27, 6.828; 235/462.22; 396/121; 250/575, 208.1, 338.1
See application file for complete search history.

(56) References Cited

U.S. PATENT DOCUMENTS

| | | | |
|---|---|---|---|
| 5,565,668 A * | 10/1996 | Reddersen et al. ..... | 235/462.22 |
| 6,614,043 B2 | 9/2003 | Hochstein | |
| 6,617,564 B2 | 9/2003 | Ockerse et al. | |
| 6,672,744 B2 | 1/2004 | DeLine et al. | |
| 6,681,163 B2 | 1/2004 | Stam et al. | |
| 6,806,452 B2 | 10/2004 | Bos et al. | |
| 6,853,897 B2 | 2/2005 | Stam et al. | |
| 6,861,636 B2 | 3/2005 | Ockerse et al. | |
| 7,586,675 B2 * | 9/2009 | Sander ................. | 359/379 |
| 2002/0056805 A1 | 5/2002 | Bos et al. | |
| 2002/0148987 A1 | 10/2002 | Hochstein | |
| 2002/0191409 A1 | 12/2002 | Deline et al. | |
| 2003/0066948 A1 | 4/2003 | Ockerse et al. | |
| 2003/0069674 A1 | 4/2003 | Stam et al. | |
| 2003/0201380 A1 | 10/2003 | Ockerse et al. | |
| 2004/0153225 A1 | 8/2004 | Stam et al. | |
| 2005/0206511 A1 * | 9/2005 | Heenan et al. ........... | 340/438 |
| 2006/0076478 A1 | 4/2006 | Johnson et al. | |
| 2007/0182816 A1 * | 8/2007 | Fox ..................... | 348/118 |

FOREIGN PATENT DOCUMENTS

| | | | |
|---|---|---|---|
| WO | 03029056 A2 | 4/2003 | |
| WO | 03029757 A2 | 4/2003 | |

* cited by examiner

*Primary Examiner*—David P Porta
*Assistant Examiner*—Yara B Green
(74) *Attorney, Agent, or Firm*—Jacox, Meckstroth & Jenkins

(57) ABSTRACT

A sensor that is photosensitive vis-à-vis at least part of the radiation in the visible range and/or in the near infrared range installed on a vehicle, the sensor being associated with an objective having a first zone that is focused to infinity and a second zone focused in near field.

24 Claims, 2 Drawing Sheets

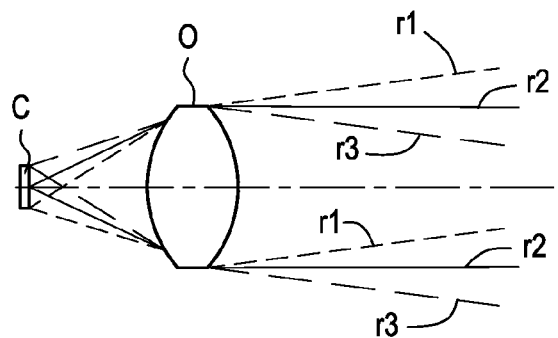
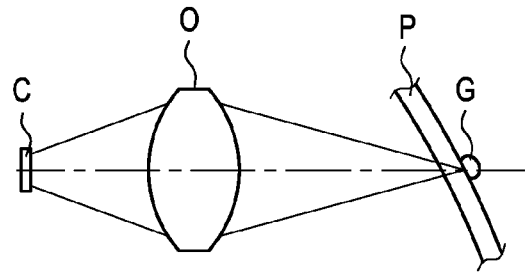
FIG.1A  FIG.1B
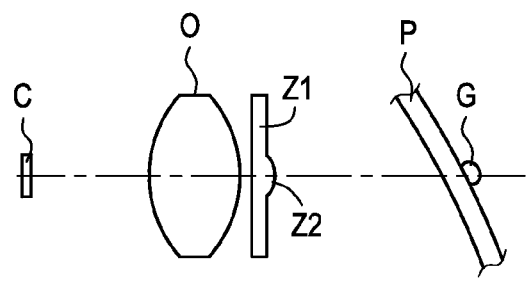
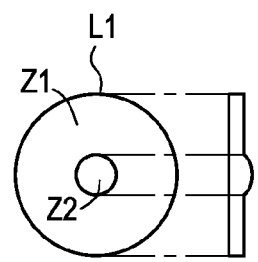
FIG.1C  FIG.3
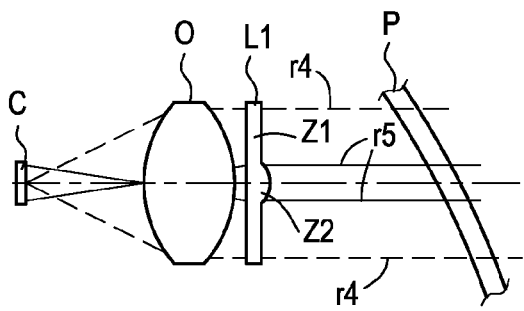
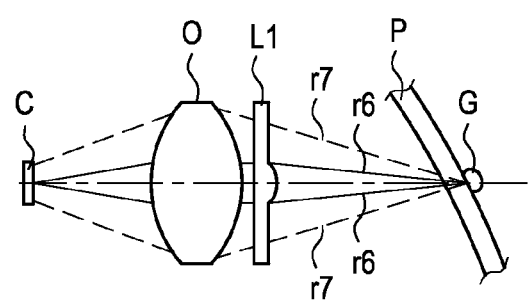
FIG.2A  FIG.2B

PHOTOSENSITIVE SENSOR IN THE AUTOMOTIVE FIELD

BACKGROUND OF THE INVENTION

1. Field of the Invention

The present invention concerns cameras equipped with sensors, for example of the CCD sensor type (charge coupling sensors), CMOS sensor type (Complementary Metal Oxide Semiconductor) or cameras of the video camera type. These sensors are grouped together in the remainder of the present text under the generic term photosensitive sensors. They supply signals representing an image that can then be processed. They are generally sensitive in the visible range and/or in the infrared range, in particular in the near infrared.

2. Description of the Related Art

This type of photosensitive sensor is being included more and more frequently in motor vehicles. The images obtained can be processed to allow the display of images on screens, for example at the dashboard or projected on the windscreen, in particular to alert the driver in the case of danger or simply to improve his visibility. The images can also make it possible to detect raindrops on the windscreen.

These images can participate in the automatic triggering of a functionality of the vehicle (alert to the driver, automatic triggering of braking, automatic triggering of the windscreen wipers in the case of the display of drops of water on the windscreen, visual or audible warning, control of certain functions of the headlight, etc).

These sensors can be used by day. They can also be used at night, and it is then possible to use their capacities to detect radiation in the infrared. In nocturnal use, these sensors thus participate for example in the "night vision" functionality (or "night vision" in English), where the images, once processed, are projected onto a display screen generally in the form of black and white images.

It can be seen by these very varied applications that it is desirable, but very difficult in practice, to use a single sensor to implement several of these applications, since the image capture parameters vary considerably according to the application.

Let us take an application concerning in particular the present invention, namely the use of a sensor for detecting any drops of water on the vehicle windscreen, in order to automatically control the functioning of the wipers: The sensor is generally installed in the vehicle close to the windscreen, for example around twenty centimeters from it, and it is therefore associated with a lens focused on the windscreen in order to be able to detect precisely the drops of water on the windscreen, their contours, their size, etc. On the other hand, if it is wished to use a sensor for taking images of the road, that is to say far-field images through the windscreen, it is necessary on this occasion to associate with the sensor a lens focused on infinity.

Use is therefore made of dedicated sensors, one per application, which increases the cost, the size and the complexity of the equipment of the vehicle, the size being not the least of the drawbacks since the space available close to the windscreen is often very limited.

SUMMARY OF THE INVENTION

The aim of the invention is then to remedy these drawbacks, in particular by proposing a novel type of sensor installed in a vehicle that can serve for several applications in a satisfactory manner.

The object of the invention is first of all a sensor that is photosensitive vis-à-vis at least part of the radiation in the visible and/or near infrared range, installed on the vehicle, the sensor being associated with a objective having a first zone that is focused to infinity and a second zone focused in near field.

"Near field" is a term known to persons skilled in the art and relates here, in particular, to a distance of around a centimeter or a few tens of centimeters (corresponding for example to a normal distance between camera and wiped windscreen area in the vehicle).

The relative sizes of the first and second zones of the objective can be adapted according to requirements.

One can thus have a majority or minority surface area with respect to the other. "Majority" and "minority" means the respective spatial extents of the zones of the objective focused differently. "Majority" means therefore that the zone of the objective that is focused to infinity (or respectively in near field) extends over more than 50% of the entry surface of the objective placed in front of the sensor.

According to one embodiment of the invention, the ratio between the surface areas of the two zones of the objective is approximately 50/50 or, more generally, in the range 70/30-60/40. The choice of the ratio will be made in particular depending on whether it is wished to favor the detection of near or far images, according to the application sought.

The invention therefore proposes to use a multi-, in particular bi-focal objective so that the sensor installed can become multi-function: methods of detecting lane edges or road verges, or detecting pedestrians or obstacles, will be able to use the portions of images taken by the sensor, sufficiently sharp by virtue of the zone of the objective focused to infinity. And a method of the type involving automatic functioning of the windscreen wipers will be able to use the portion of images taken at a very short distance, on the windscreen, through the zone of the objective focused on the windscreen. It is thus possible to have an image that is the superimposition of images taken in the distance with the adapted focal distance, and images taken close by with a shorter focal distance. It may be useful, optionally, to improve the contrast of at least one of the images or of the superimposition of images thus obtained by a known processing of the contrast reinforcement type.

Advantageously, the objective comprises a plurality of optical elements of the lens type, in particular grouped together in one or more trains of lenses in a known manner, including an optical element defining the zone and disposed in or substantially close to an opening pupil plane of the objective. This particular arrangement guarantees that any point on the far-field image (the image of the road) on the one hand and that any point on the near-field image (the image of the windscreen) on the other hand is formed by an equivalent quantity of rays (equivalent portions of the opening pupil).

This optical element, once this condition is fulfilled, can be disposed at any point on the objective, which is generally a complex combination of lenses. Two configurations are envisaged, in particular: either it is the first optical element from the entrance of the objective, or it is an optical element disposed just upstream. "Entrance" of the objective means the face of the objective turned towards the image to be taken, towards the outside therefore, and "upstream" means an arrangement in front of the objective with respect to the image to be detected.

According to one embodiment, this optical element is a lens for the main part neutral on an optical level and locally focused in near-field. It may in particular be a lens with parallel entry and exit faces and having locally an exit face substantially at least partially convex.

According to another embodiment, this optical element is the first lens of the objective, the entry lens thereof, the zone focused in near field being obtained by a local modification of the curvature of the exit face of the lens, in particular with a convex part different from the curvature of the rest of the exit face.

In either case, the modification may be in the form of a spherical or aspheric lens portion.

Advantageously, the zone focused in near field of the exit face of the optical element is situated in the central part of the element.

In concrete terms, the objective can be a train of lenses, the first lens of which is modified or associated with a modified lens, the lenses all having a substantially circular contour, and the modification being a zone centered on the lens face in question, and protruding with respect to the curvature or absence of curvature thereof.

The sensor and its objective thus described can be used in a method of detecting drops of rain on a windscreen of the vehicle, but also for the capture of images of scenes of the road through the windscreen of the vehicle.

The invention also concerns a method of detecting drops of rain on a windscreen by means of a sensor photosensitive vis-à-vis at least part of the radiation in the visible and/or near infrared range, the sensor being associated with an objective having a first majority zone that is focused at infinity and a second minority zone with a shorter focal distance.

The invention also concerns an image processing device installed on a motor vehicle, using at least one sensor as described above.

The invention also concerns an image processing method using the signals received by such a sensor installed on a motor vehicle.

The invention also concerns the motor vehicle provided with such a sensor.

These and other objects and advantages of the invention will be apparent from the following description, the accompanying drawings and the appended claims.

BRIEF DESCRIPTION OF THE DRAWINGS

The invention will be detailed below with non-limitative examples, with the help of the following figures:

FIGS. 1A, 1B and 1C show a schematic representation of sensor objectives concerning the invention, FIGS. 2A and 2B show a schematic representation of a sensor with modified objective according to the invention seen in section, depending on whether an image of a road scene in the distance (FIG. 2A) is considered or a drop of water on the windscreen (FIG. 2B), FIG. 3 is a representation of the modified lens of the objective according to the previous figure, seen in front view and side view.

DESCRIPTION OF THE PREFERRED EMBODIMENTS

All these figures are extremely schematic and are not necessarily to scale, for more clarity.

FIG. 1A shows a standard sensor C, of the CCD type, and associated with an objective O focused to infinity in order to capture images in the distance. Sensor C and objective O are disposed behind the wiped area of the windscreen of a motor vehicle, at approximately ten to twenty centimeters from it. The objective O comprises a train of lenses, it has been represented by a single lens. Rays entering the objective in order to reach the receiving surface of the sensor C have been traced: The rays r1 are situated at the top, r2 at the middle part and r3 at the bottom part of the image.

FIG. 1B adds to the previous figure the symbolic representation of a windscreen P and a drop of water G on it. With such an objective, this drop of water G on the windscreen P is not correctly imaged on the sensor C and is therefore not detectable by image processing.

As depicted in FIG. 1C, according to the invention there is added to the objective O an additional lens L1 that is mainly neutral optically, except at its central part where it has a zone Z2 focused in near field, with an at least partially convex shape: an objective O is obtained with a zone Z1 with a focal distance to infinity "surrounding" a zone Z2 in near field.

FIG. 3 presents the exit face of the modified lens L1: the zone focused in near zone Z2 is circular in shape, disposed on the circular exit face of the lens L1, concentrically. According to an example embodiment, the zone Z1 and the zone Z2 are of similar sizes (once projected onto a vertical plane according to the figure). The modified zone Z2 is here convex in shape, substantially spherical. Alternatively, the zone Z2 can be aspheric.

As shown in FIG. 2A, this lens L1 is situated in an opening pupil plane of the objective O. This lens L1 does not modify the routing of the rays imaging objects at a great distance, except in the center of the image. However, the rays that pass through the objective O in this central part Z2 are diverted so that they no longer image the center of the image.

Figure 4A:
FIGS. 4A, 4B and 4C are images taken in the distance according to the invention.
Figure 4B:
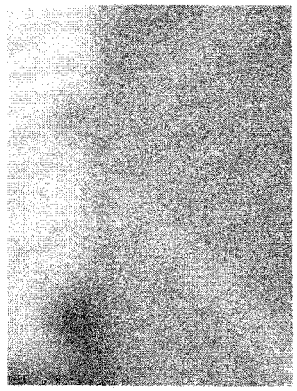
Figure 4C:
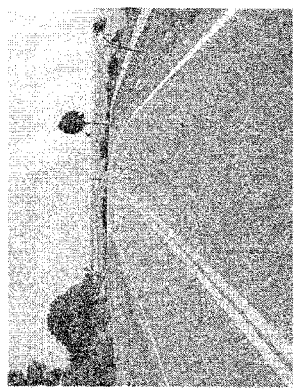

The result, shown in FIG. 4C, is an image superimposing:
a very sharp image of the road scene, depicted in FIG. 4A (and corresponding to the rays r4 passing at the periphery as shown in FIG. 2A, that is to say passing through the zone Z1 with a focal distance at infinity)
and a very fuzzy image (corresponding to the rays r5 passing at the center as shown in FIG. 2A, that is to say the rays passing through the reduced focal distance zone Z2 of the lens L1).

Turning now to the drop of water G: this is clearly imaged by the rays passing through the zone Z2 of the lens L1, these are the rays r6 shown in FIG. 2B. Its image is on the other hand very fuzzy for the rays r7 passing through Z1: these are the rays r7 shown in FIG. 2B.

Figure 5A:
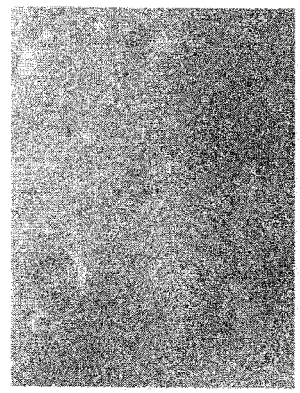
FIGS. 5A, 5B and 5C are images taken at a short distance according to the invention.
Figure 5B:
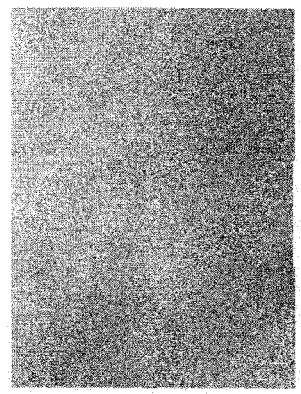
Figure 5C:
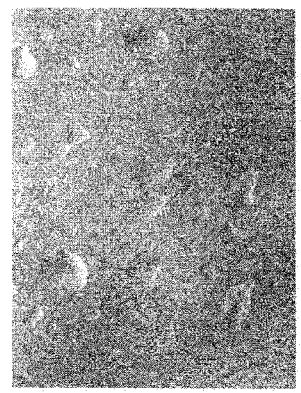

The result, shown in FIG. 5C, is an image superimposing
a very sharp image of the drop of water G: FIG. 5A,
and a very fuzzy image: FIG. 5B.

Figure 6:
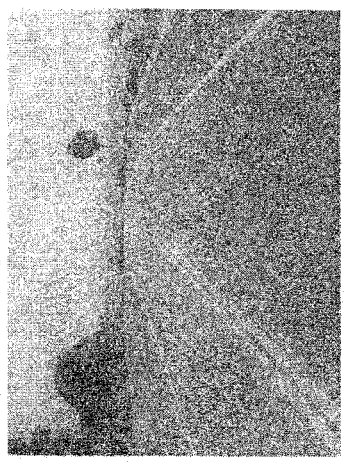
FIG. 6 is an image superimposing an image taken in the distance and taken at a short distance according to the invention.

The sensor-objective system according to the invention thus "looks" both in the distance and at a very short distance, the global image being depicted in FIG. 6 and being the sum of the FIGS. 4C and 5C. It is verified from FIG. 6 that the image obtained affords great sharpness both of the image of the road in the distance and of the drops of water G on the windscreen P.

An image processing of the contrast reinforcement processing type can be envisaged but is optional.

The invention therefore indeed makes it possible to share the same camera and the same sensor for multiple functions, by virtue of a modified objective. There is thus no longer any obligation to have a sensor dedicated to the detection of rain.

The invention thus finds an application in the automotive field, but is also applicable to any other field where a sensor is needed that is effective both close by and in the distance, in particular in any other type of locomotion means.

The images obtained according to the invention can then be the subject of various processing operations with a view to their use.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A photosensitive sensor vis-à-vis at least part of the radiation in the visible and/or near infrared range installed on a vehicle, wherein said photosensitive sensor is associated with an objective having a first zone that is focused to infinity so that said photosensitive sensor can capture a first image, and a second zone focused in near field so that said photosensitive sensor can capture a second image, said objective having at least one train of lenses for forming said first and second zones, and said photosensitive sensor senses said first and second images using each of said first and second zones, respectively, said objective having an exit face having a convex face having a convex shape associated with said second zone and having a surface associated with said first zone that does not comprise the same convex shape as said convex face;
said photosensitive sensor cooperating with said objective and generating a superimposed image resulting from a superimposition of said first image and said second image whereby said superimposed image comprises a sharp or focused image of both said first and second images;
said superimposed image being used to control a function on the vehicle or to operate the vehicle.

2. The photosensitive sensor according to claim 1, wherein said objective comprises a plurality of optical elements of a lens type, in particular grouped together in said at least one train of lenses, including an optical element defining said second zone and disposed in or substantially close to an opening pupil plane of said objective.

3. The photosensitive sensor according to claim 1, wherein an optical element defining a zone is a first optical element from an entry of said objective, or is an optical element disposed just upstream thereof.

4. The photosensitive sensor according to claim 3, wherein said optical element defining said zone is a first lens of said objective, said zone being obtained by a local modification of a curvature of an exit face of a lens, in particular with a convex part different from said curvature of a rest of said exit face.

5. The photosensitive sensor according to claim 1, wherein an optical element defining a zone is a lens mainly neutral on an optical level and having locally the required focusing.

6. The photosensitive sensor according to claim 1, wherein an optical element mainly neutral on an optical level is of a lens type with parallel entry and exit faces, and having locally an exit face substantially at least partially convex, in particular of a spherical or aspheric type.

7. The photosensitive sensor according to claim 1, wherein a zone of focal distance of an exit face of an optical element is situated in a central part of said optical element.

8. The photosensitive sensor according to claim 1, wherein said photosensitive sensor is used in a method of detecting drops of rain on a windscreen of said vehicle.

9. The photosensitive sensor according to claim 1, wherein said photosensitive sensor is also used for the capture of images of scenes of a road through a windscreen of said vehicle.

10. A motor vehicle, wherein said motor vehicle is provided with said photosensitive sensor according to claim 1.

11. The photosensitive sensor according to claim 1, wherein said function is to alert a driver of danger, to improve visibility or to detect raindrops on the windscreen.

12. A method of detecting drops of rain on a windscreen, said method comprising the steps of:
sensing at least part of the radiation in the visible and/or near infrared range with a photosensitive sensor;
situating said photosensitive sensor near an objective having a first zone that is focused to infinity so that said photosensitive sensor can capture a first image, and a second zone focused in a near field so that said photosensitive sensor can capture a second image, said objective having at least one train of lenses for forming said first and second zones, and said photosensitive sensor senses said first and second images using each of said first and second zones, respectively, said objective having an exit face having a convex face having a convex shape associated with said second zone and having a surface associated with said first zone that does not comprise the same convex ship as said convex face;
said photosensitive sensor cooperating with said objective and generating a superimposed image resulting from a superimposition of said first image and said second image whereby said superimposed image comprises a sharp or focused image of both said first and second images;
said superimposed image being used to control a function on the vehicle or to operate the vehicle.

13. The method as recited in claim 12, wherein said method further comprises the step of:
using signals received by said photosensitive sensor installed on a motor vehicle.

14. The photosensitive sensor according to claim 12, wherein said function is to alert a driver of danger, to improve visibility or to detect raindrops on the windscreen.

15. An image capturing system for use in a vehicle comprising:
a photosensitive sensor for capturing an image of a plurality of zones at a plurality of focal distances from said photosensitive sensor; and
a single lens comprising a plurality of optical elements adapted to be focused on said plurality of zones so that said photosensitive sensor can capture a first image and a second image, said single lens having at least one train of lenses for forming first and second zones, and said photosensitive sensor senses said first and second images using each of said first and second zones, respectively, an objective having an exit face having a convex face having a convex shape associated with said second zone and having a surface associated with said first zone that does not comprise the same convex shape as said convex face;
said photosensitive sensor cooperating with said objective and generating a superimposed image resulting from a superimposition of said first image and said second image whereby said superimposed image comprises a sharp or focused image of both said first and second images;
said superimposed image being used to control a function on the vehicle or to operate the vehicle.

16. The image capturing system as recited in claim 15, wherein said single lens comprises a first portion for enabling said photosensitive sensor to focus on a near zone and a second portion for enabling said photosensitive sensor to focus on a far zone.

17. The image capturing system as recited in claim 16, wherein said near zone comprises a surface of a windscreen.

18. The image capturing system as recited in claim 16, wherein said far zone is a roadway surface in front of the vehicle.

19. The image capturing system as recited in claim 16, wherein said single lens comprises sides that do not have the same shape or contour.

20. The image capturing system as recited in claim 17, wherein said far zone is a roadway surface in front of the vehicle.

21. The photosensitive sensor according to claim 15, wherein said function is to alert a driver of danger, to improve visibility or to detect raindrops on the windscreen.

22. A photosensitive sensor vis-à-vis at least part of the radiation in the visible and/or near infrared range installed on a vehicle, wherein said photosensitive sensor is associated with an objective having a first zone that is focused to infinity so that said photosensitive sensor can capture a first image and a second zone focused in near field so that said photosensitive sensor can capture a second image, wherein the objective comprises an optical element having a local neutral zone and a convex local exit face;

said photosensitive sensor cooperating with said objective and generating a superimposed image resulting from a superimposition of said first image and said second image whereby said superimposed image comprises a sharp or focused image of both said first and second images;

said superimposed image being used to control a function on the vehicle or to operate the vehicle.

23. The photosensitive sensor according to claim 22, wherein said function is to alert a driver of danger, to improve visibility or to detect raindrops on the windscreen.

24. A photosensitive sensor vis-à-vis at least part of the radiation in the visible and/or near infrared range installed on a vehicle, wherein said photosensitive sensor is associated with an objective having a first zone that is focused to infinity so that said photosensitive sensor can capture a first image and a second zone focused in near field so that said photosensitive sensor can capture a second image, wherein the objective comprises an optical element having:

locally parallel entry and exit faces; and locally a convex exit face;

said photosensitive sensor cooperating with said objective and generating a superimposed image resulting from a superimposition of said first image and said second image whereby said superimposed image comprises a sharp or focused image of both said first and second images;

said superimposed image being used to control a function on the vehicle or to operate the vehicle.

\* \* \* \* \*